United States Patent [19]

Spector

[11] Patent Number: 4,568,521
[45] Date of Patent: Feb. 4, 1986

[54] SOLAR-POWERED AROMA GENERATOR

[76] Inventor: Donald Spector, 380 Mountain Rd., Union City, N.J. 07087

[21] Appl. No.: 592,915

[22] Filed: Mar. 23, 1984

[51] Int. Cl.[4] .................................................. A62B 7/08
[52] U.S. Cl. ...................................... 422/124; 136/246; 136/291; 422/4; 422/105
[58] Field of Search ........................ 422/4, 124, 5, 122, 422/123, 105; 136/244, 245, 246, 291

[56] References Cited

U.S. PATENT DOCUMENTS

| | | | |
|---|---|---|---|
| 2,050,773 | 8/1936 | Wall | 422/124 |
| 3,353,191 | 11/1967 | Dahly | 136/291 |
| 3,948,445 | 4/1976 | Andeweg | 422/125 |
| 4,346,059 | 8/1982 | Spector | 422/4 |
| 4,379,324 | 4/1983 | Thompson | 136/291 |
| 4,444,720 | 4/1984 | Mayer | 422/4 |

*Primary Examiner*—Barry S. Richman
*Assistant Examiner*—Titus B. Ledbetter, Jr.
*Attorney, Agent, or Firm*—Michael Ebert

[57] ABSTRACT

An aroma generator that is automatically activated when one turns on an electric light bulb in the room in which the generator is installed, the generator then functioning to discharge an air current into the room conveying an aromatic vapor which modifies the prevailing atmosphere. Included in the generator is a motor-driven fan that forces air through an air permeable cartridge containing an aroma supply, the motor being powered by a solar cell assembly mounted adjacent the bulb. The arrangement is such that when the bulb is switched on, the resultant cell output is sufficient to power the motor and activate the generator, the cell output, in response to ambient light being insufficient for this purpose, whereby the operation of the generator is coordinated with that of the bulb without any wire connection therebetween.

6 Claims, 5 Drawing Figures

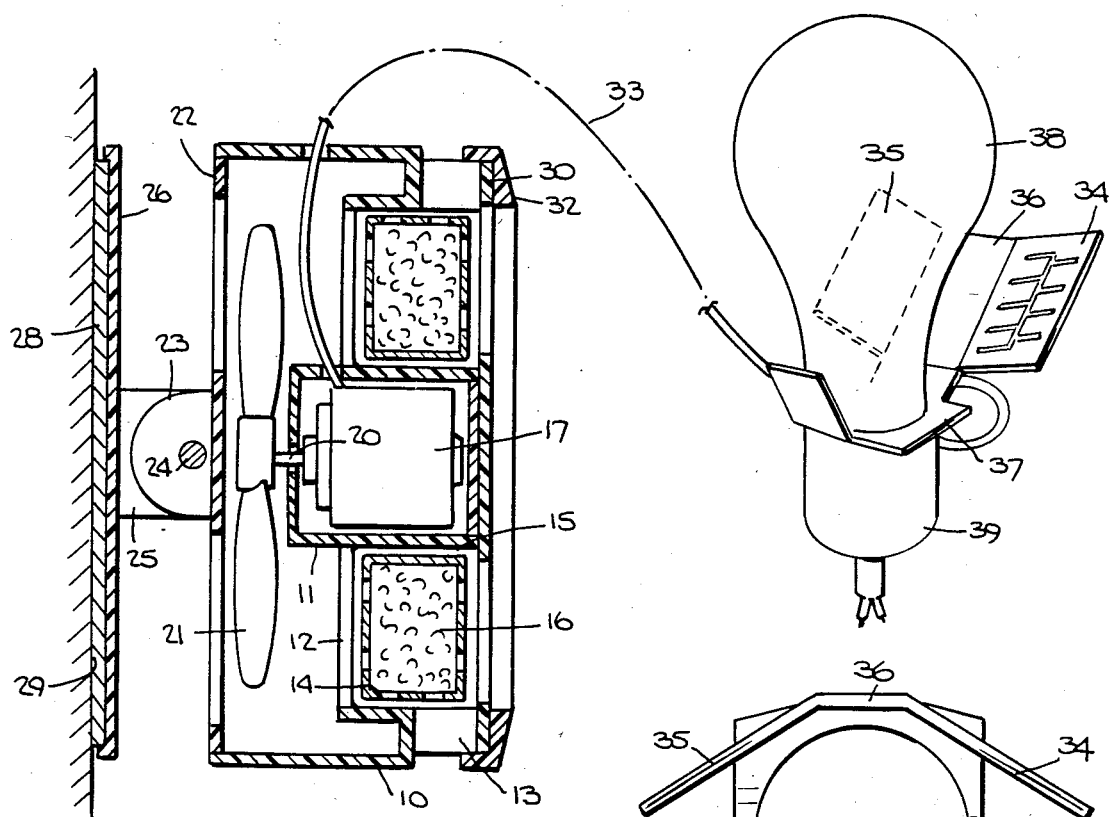
Fig. 1.
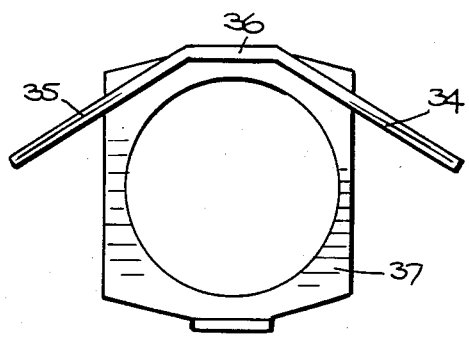
Fig. 4.
Fig. 2.
Fig. 5.
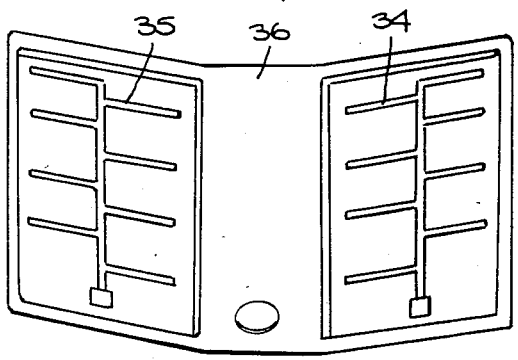

SOLAR-POWERED AROMA GENERATOR

BACKGROUND OF INVENTION

Field of Invention

This invention relates generally to aroma generators, and more particularly to a fan-operated aroma generator powered by energy obtained from a solar cell assembly and rendered active automatically when the light flux incident to the assembly exceeds a predetermined level, the generator being deactivated when the light falls below that level.

In order to modify the atmosphere of a room, it is known to discharge therein air fresheners, deodorizers or aromatic vapors which function to mask or supplant the prevailing odor and render it more agreeable. As used herein, the term "aroma" is generic to all such air modifiers; it is not limited to pleasing fragrances or perfumes, and encompasses various scents or odors that act in some way to modulate the atmosphere of a room.

Certain types of air fresheners are appropriate to heavily-used lavatories and bathrooms, or rooms whose atmosphere is contaminated by tobacco smoke or cooking odors. In other instances, as in bedrooms, a perfumed environment may be more suitable. Hence the effect sought when modifying an atmosphere, depends on its initial state and the desired state.

To satisfy the requirements for improving or modifying the atmosphere to create a more agreeable environment, it is known, as in the patent to Koritz, U.S. Pat. No. 4,102,656, to blow air through a filter saturated with an aromatic liquid compound, use being made of a motor-driven fan for this purpose. Along similar lines, is the air purifier disclosed in the Madjar U.S. Pat. No. 4,078,891 in which a blower forces air through a filter impregnated with a disinfectant or perfume.

The above-identified patents make use of fan motors energized from a power line, whereas in the Corris U.S. Pat. No. 3,990,848, the fan which forces air through a porous cartridge containing a room deodorizer or germicide is battery-operated.

In order to activate the air purifier at different times and for different intervals, the above-identified Madjar patent provides a timed switch for this purpose. Also of interest is the patent to Boydjieff, U.S. Pat. No. 2,614,820, showing a portable vapor-projecting device for perfuming the air and including a timer switch to drive the fan motor for a preset interval. But the timing of this operation is preset and does not depend on unpredictable random actions. Thus in the case of the typical bathroom, there is no way of knowing in advance when the bathroom will be occupied or for how long.

One could, of course, provide an aroma generator of the types disclosed in the above-noted patents with a conventional power switch, so that each time a person enters a room in which the generator is installed, he could turn on the generator, and before leaving the room he could switch it off.

There are, however, several drawbacks incident to the use of such conventional control switches. Thus when a home bathroom is used by a guest, the guest may not know that an aroma generator is installed therein, particularly if the generator is so designed as to assume the appearance of an ornamental object rather than a utilitarian device.

But even if the guest or a resident in the home knows that an aroma generator is installed in the bathroom and turns it on when entering the room, he may thereafter forget to turn it off when leaving. Should the aroma generator then continue to operate, the accumulated amount of aroma then exuded into the atmosphere may be so great as to cause it to spill into adjacent areas or rooms where the bathroom aroma is altogether inappropriate. Moreover, continuous operation of the aroma generator will shorten the effective life of whatever cartridge or pad is used as the aroma supply.

A more serious drawback of aroma generators which derive their power from a high-voltage power line and therefore have to be plugged into the line, is that such devices represent a possible electrical hazard in a bathroom where water in some form is inevitably present, and where an individual standing on a wet floor or in a tub, should he then touch the aroma generator, may receive an electrical shock.

It is for this reason that battery-operated aroma generators are preferable for bathroom environments. But while batteries have a long life when used for powering electrical devices which have no internal mechanisms, such as a transistor radio, when batteries are used to energize a motor, their lives are normally relatively short. As a consequence, the aroma generator can only be operated for a few hours before it becomes necessary to replace the batteries.

SUMMARY OF INVENTION

In view of the foregoing, the main object of this invention is to provide a fan-operated aroma generator powered from a solar cell assembly, the generator being activated automatically when a light bulb in the room in which the generator is installed is switched on, the generator being deactivated when the light is switched off.

More particularly, an object of the invention is to provide an aroma generator of the above type which is mountable on a wall in a room, the solar cell assembly being attachable to the light bulb whereby the action of the generator is coordinated with that of the bulb.

A significant feature of the invention lies in the use of an air-permeable cartridge filled with fragrance beads which exude an aroma at a relatively high rate when an air current is blown therethrough by the fan and which continues to exude an aroma at a much lower rate when the fan is deactivated whereby the aroma generator maintains a low level of fragrance in the room which is stepped up to a high level only when the fan is activated.

Also an object of the invention is to provide a cartridge type aroma generator in which the cartridge, when exhausted, may readily be replaced by a fresh cartridge yielding the same or a different aroma.

Among the advantages of the invention are the following;

A. Because it makes use of a low-voltage solar cell assembly, no need exists to replace batteries or to plug in the generator, thereby avoiding electrical hazards.

B. Because the solar cell assembly is physically attached to the light bulb, the solar cell yields a large output only when the bulb is turned on, the output produced in response to ambient natural light being insufficient to energize the fan motor.

C. The orientation of the aroma generator relative to the wall on which it is mounted is adjustable to a position affording optimum effects.

Briefly stated, these objects are attained in an aroma generator that is automatically activated when one turns on an electric light bulb in the room in which the generator is installed, the generator then functioning to discharge an air current into the room conveying an aromatic vapor which modifies the prevailing atmosphere. Included in the generator is a motor-driven fan that forces air through an air permeable cartridge containing an aroma supply, the motor being powered by a solar cell assembly mounted adjacent the bulb. The arrangement is such that when the bulb is switched on, the resultant cell output is sufficient to power the motor and activate the generator, the cell output, in response to ambient light being insufficient for this purpose, whereby the operation of the generator is coordinated with that of the bulb without any wire connection therebetween.

OUTLINE OF DRAWINGS

For a better understanding of the invention as well as other objects and further features thereof, reference is made to the following detailed description to be read in conjunction with the accompanying drawings, wherein:

FIG. 1 is a sectional view of an aroma generator in accordance with the invention, the generator including a solar cell assembly which is shown attached to a light bulb;

FIG. 2 is a side view of the aroma generator when mounted on a wall;

FIG. 4 is a top view of the solar cell assembly; and

FIG. 5 is a front view of the solar cells apart from the assembly.

DESCRIPTION OF INVENTION

Figure 3:
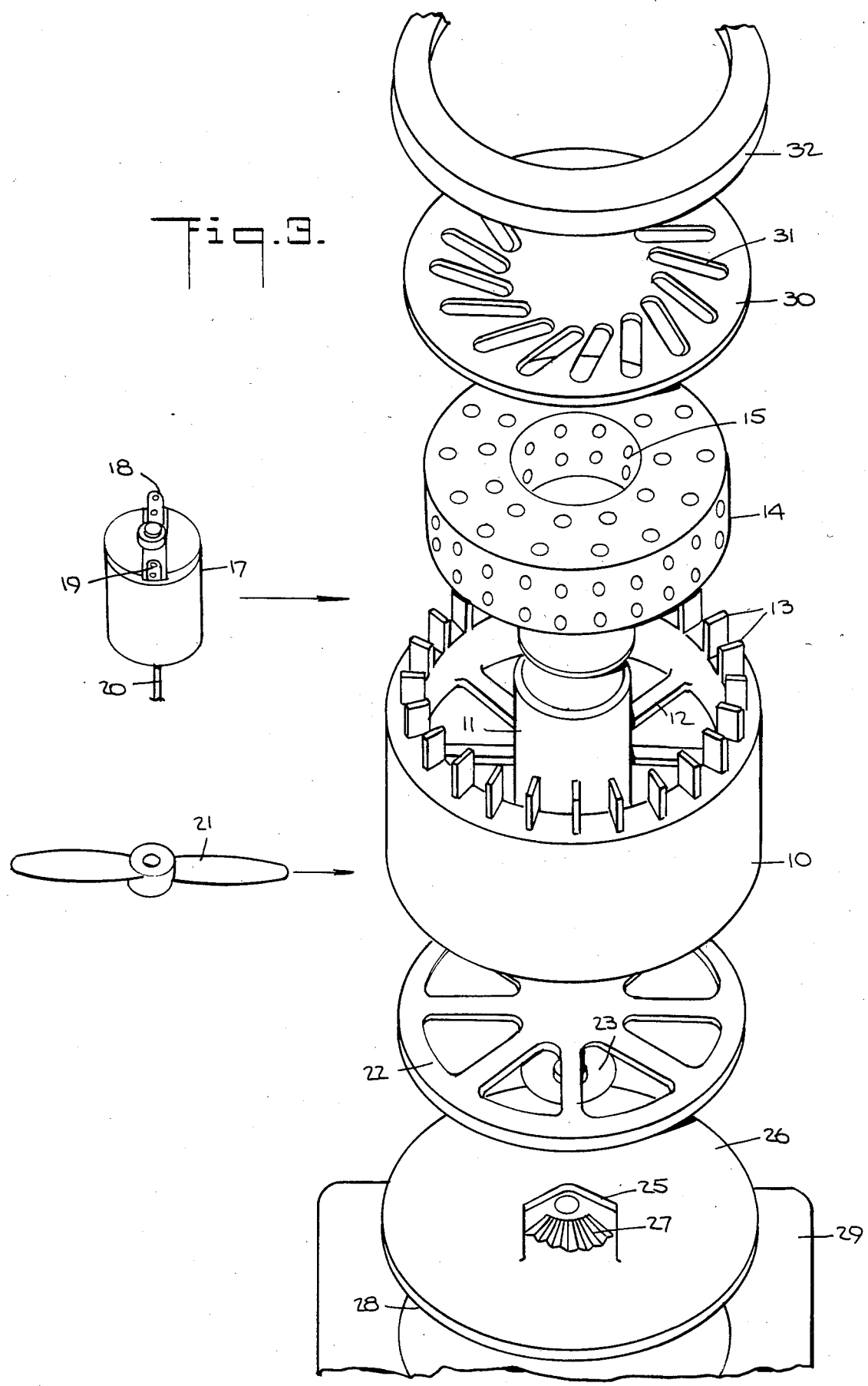
FIG. 3 is an exploded view of the aroma generator.

Referring now to FIGS. 1 and 3, there is shown an aroma generator in accordance with the invention, the generator including a cylindrical main body 10 having a tubular socket 11 supported coaxially therein by a spider 12. Projecting from the front edge of the body is a circular array of fins 13. This structure and all other components are preferably molded from synthetic plastic material having good physical properties, such as polypropylene or polyvinyl chloride.

Seated on spider 12 within main body 10 is a disposable fragrance cartridge 14 having a circular center hole 15 through which socket 11 extends. The cartridge walls are foraminated so that the cartridge is permeable to air. The cartridge is filled with a charge of fragrance beads 16 of the type commonly used in commercial air fresheners, the fragrance being exuded from the beads at a rate determined by air flow through the air permeable cartridge. Thus in the absence of forced air flow, the rate of exudation is relatively slow and the cartridge has an extended effective life.

The invention is not limited to fragrance beads, for any aromatic supply may be used in the cartridge, such as a porous pad impregnated with a liquid fragrance. Nor is the invention limited to any particular aroma, and use may be made of deodorizers, air fresheners, perfumes or any other atmosphere-modifying agent.

Received within tubular socket 11 is a miniature low-voltage direct-current motor 17 in cylindrical form having a pair of terminals 18 and 19 at one end and a central shaft 20 projecting from the other end. Supported on this shaft is a fan propeller 21 which rotates within the rear end of body 10 behind spider 12, the back being closed by a closure plate 22 having a spoked wheel formation.

Closure plate 22 is provided at its rear with a semicircular tab 23 which projects from the hub of the plate. Tab 23 is attached by a pivot pin 24 to a stud 25 projecting from the front face of a mounting disc 26. One side of stud 25 is provided with a radial array of ridges 27 which frictionally engage the corresponding side of swivel tab 23 to resist displacement of the swivel.

The rear face of mounting disc 26 has attached thereto a layer 28 of pressure-sensitive adhesive material, making it possible to mount the generator at any desired site on a wall 29, as shown in FIG. 3. Because of the swivel, the generator may be oriented relative to the wall to optimize its effectiveness. Thus if the generator is mounted at an elevated position on the wall, it may then be tilted down to direct the aroma toward the occupants of the room.

The front face of cartridge 14 is covered by a disc 30 having an array of vents 31 therein. This disc is held in place by a cover ring 32 which engages the upper portions of fins 13 on the main body 10, the lower portions being exposed to permit aromatic vapors to be discharged omnidirectionally from the circular periphery of the cartridge.

The terminals 18 and 19 of motor 17 are connected by a flexible extension line 33 to a pair of solar cells 34 and 35 mounted on the oppositely-inclined wings of the baffle 36 of the color cell assembly. Baffle 36 is supported in an upright position on an insulating card 37 having a circular opening whose diameter is substantially the same as that of the base portion of a standard electric light bulb 38. Bulb 38 is screwed into an electrical socket 39.

Electric light bulb 38 can be any accessible bulb in the room in which the aroma generator is installed. In installing the solar cell assembly, one first screws out the bulb from its socket and then inserts the bulb into the opening of card 37. By then screwing the bulb back into the socket, the card is then locked in place. When so installed, the two solar cell wings of the assembly are disposed on either side of the bulb so as to intercept the light emitted therefrom.

The two solar cells may be connected in series or in parallel relation, depending on the voltage rating of the motor. If, for example the d-c motor has a three volt rating and the cells each yield one and one-half volts, the cells are then connected in series to double the output voltage; but if the motor has a one and one-half volt rating, the cells are then connected in parallel to double the cell capacity.

Since the motor is lightly loaded by the fan, the power capacity of the motor may be very small and require only a few watts of energy to operate. However, the relationship of the solar cell assembly to the motor power requirements are such that only when the cells are in direct proximity to the light bulb (say, 60 watts), will sufficient output be produced to energize the motor.

Thus while the ambient natural light in the room will result in some solar cell output, the relationship is such that this output is insufficient to energize the motor. As a consequence, when the light is turned off, the generator exudes only a low level of aroma, for the fan is not operative and no air is then forced through the cartridge. This low level in the static condition of the generator acts to prime the atmosphere of the room, but little aroma seepage from the room takes place even if the door is open; for the fragrance in the atmosphere is diluted. But when one enters the room and turns on the light, then the motor is automatically energized and the fan drives a current of air through the cartridge, which current is discharged into the atmosphere and carries with it an aromatic vapor to step up the fragrance in the room to a high level. The moment, however, the light is turned off, this discharge is discontinued.

While there has been shown and described a preferred embodiment of a solar-powered aroma generator in accordance with the invention, it will be appreciated that many changes and modifications may be made therein without, however, departing from the essential spirit thereof. Thus instead of having an extension line from the solar cell assembly to the generator, the solar cell assembly may be mounted directly on the housing of the generator, in which case it becomes necessary to install the generator in close proximity to a light bulb.

I claim:

1. In combination with a switch-controlled electric light bulb having a threaded plug and a threaded socket disposed in a room which is also subject to natural ambient light, a switchless aroma generator installed in the room which is automatically activated only when the electric light bulb is switched on, the activated generator functioning to discharge an air current into the room which conveys an aromatic vapor to modify the atmosphere prevailing therein, said generator comprising:

A an air-permeable cartridge containing an aroma supply which is exuded into the atmosphere at a relatively rapid rate as an air current is forced through the cartridge;

B a fan driven by a low-voltage, direct-current motor having predetermined power requirements, the fan being arranged to force an air current through said cartridge;

C a housing incorporating said cartridge and said motor-driven fan, said housing comprising means for mounting it on a wall in said room; and D a solar cell assembly producing a direct-current output placed in close proximity to said bulb in said room and irradiated thereby when the bulb is switched on, said assembly being connected to said motor to supply power thereto, the electrical relationship of said assembly to said motor being such that the cell output is sufficient to power said motor only when the bulb is switched on to irradiate the assembly, and is insufficient when the bulb is switched off and the cell output then depends on ambient light in the room, whereby the operation of the generator is coordinated with that of the bulb despite the absence of a wired connection therebetween and an aroma is generated only when the bulb is switched on.

2. The combination as set forth in claim 1, wherein said aroma supply is constituted by fragrance beads.

3. The combination as set forth in claim 1, wherein said housing is constituted by a cylindrical main body having a tubular socket supported coaxially therein by a spider, said motor being in cylindrical form and being received in said socket, said cartridge being in a toroidal form having a hollow core and being seated on said spider within said body, the tubular socket extending through the hollow core of the cartridge, said motor having a shaft extending beyond said spider and having said fan attached thereto which rotates within said body.

4. The combination as set forth in claim 1, wherein said assembly is attached to the exterior of said housing.

5. The combination as set forth in claim 1, wherein said solar cell assembly is constituted by an insulating card having a hole therein, through which is insertable, the threaded plug of the bulb, so that as the plug is screwed into its socket the card is then locked in place; and a baffle supported at an upright position on the card for carrying at least one solar cell at a position in close proximity to the bulb.

6. The combination as set forth in claim 5, wherein said baffle is provided with a pair of oppositely-inclined wings to carry a pair of solar cells on opposite sides of the bulb.

* * * * *